United States Patent [19]

Eagan

[11] Patent Number: 5,445,026
[45] Date of Patent: * Aug. 29, 1995

[54] ELECTRONIC INSTRUMENT FOR LOCATING AND DIAGNOSING ENGINE SOUNDS

[76] Inventor: Chris S. Eagan, 670 Eldorado La., Las Vegas, Nev. 89123

[*] Notice: The portion of the term of this patent subsequent to Jul. 25, 2012 has been disclaimed.

[21] Appl. No.: 75,790

[22] Filed: Jun. 14, 1993

[51] Int. Cl.6 .................. G01N 29/00; G01H 1/00
[52] U.S. Cl. ..................... 73/591; 73/40.5 A; 73/587
[58] Field of Search ............ 73/591, 457, 40.5 A, 73/660, 661, 587; 181/131; 381/58, 67

[56] References Cited

U.S. PATENT DOCUMENTS

| 2,008,934 | 7/1935 | Smith | 73/40.5 A |
| 2,396,935 | 3/1946 | Walstrom | 73/40.5 A |
| 4,287,581 | 9/1981 | Neale, Sr. | 73/40.5 A |

FOREIGN PATENT DOCUMENTS 2539507  7/1984  France ............... 73/40.5 A

OTHER PUBLICATIONS

McGraw-Hill Encyclopedia of Science & Technology, 1977, V. 12, p. 202 & V. 12, pp. 575-576.
A E International, "LD-180 Portable, Highly Sensitive and Highly Accurate Leak Detector" Sep. 1992.
Physical Acoustics Corp., "5100 Series Leak Monitoring & Detection Systems", 1984.

*Primary Examiner*—Hezron E. Williams
*Assistant Examiner*—Christine K. Oda
*Attorney, Agent, or Firm*—Philip D. Junkins

[57] ABSTRACT

An acoustic signal and sound diagnostic instrument, for use by a professional automotive engine or industrial machinery maintenance operator, which is capable of locating and discriminating automotive engine and industrial machinery abnormalities. The instrument includes an acoustic transducer microphone, located at the forward end of an elongated deformable, semi-rigid probe arm, for detecting and converting acoustic signals and sounds into electromagnetic signals and an electronics housing conformed to be held in the hand of the maintenance operator with the housing mechanically supporting the probe arm at its rearward end. Pre-amplifier circuitry within the housing is electrically coupled to the transducer microphone and to range selector circuitry for selecting sound level ranges respecting the electromagnetic signals. A decibel meter, mounted to the exterior of the housing, is electrically interconnected to the pre-amplifier for visually indicating changes and peaks in the sound levels detected by the transducer microphone. Operational audio amplifier circuitry within the housing is electrically interconnected to the pre-amplifier circuitry for converting the electromagnetic signals into secondary acoustic signals that may be listened to by the operator through an earphone headset electrically interconnected to the audio amplifier. The instrument is energized by a battery power supply contained within the housing.

11 Claims, 2 Drawing Sheets

ELECTRONIC INSTRUMENT FOR LOCATING AND DIAGNOSING ENGINE SOUNDS

BACKGROUND OF THE INVENTION

1. Field of the Invention

The present invention relates to a method and instrumentation for detecting, locating and diagnosing sounds generated by internal combustion engines and other machinery having rotating and moving parts. More particularly, the invention is directed to electronic diagnostic instrumentation for locating the source and cause of trouble indicating sounds in engines and machinery having rotating and moving parts.

2. Description of The Prior Art

Internal combustion engines, diesel engines, generators, compressors, pumps and numerous other types of machinery having rotating and moving parts generate a multiplicity of acoustic signals and sounds which, in combination, are referred to as engine or machinery noise. This is particularly true of automotive engines. Individual sound components of automotive engine noise, when separated, may be used to detect the existence, location and cause of an engine abnormality such as a piston knock, valve clatter, pressure leak, bearing and bushing failure, broken or chipped gear teeth or frictional abrasion. Further, sound components of the engine's environment may indicate exhaust manifold leaks, wind and water leaks, and pressure and vacuum leaks. Thus, for the proficient auto mechanic it is necessary to be able to discriminate between the acoustic signals and sounds forming the noise pattern of operating engines and engine environments and to locate the source of and cause of such signals and sounds.

In the past a number of methods have been utilized to accomplish sound discrimination and cause in internal combustion engines and other types of machinery. Most simply and basically, the auto or other mechanic has used his or her ears to listen for particular types of sound such as engine and engine accessory knocking, clinking, clattering, screeching and the like, and to move an ear toward or away from various areas of the operating engine so as to detect the increase or decrease in level of a particular sound or signal. The source of the particular knock, clink or clatter sound is thus determined by searching for the general area of the engine from which the sound appears (by hearing sense) to be emanating with the greatest intensity. This crude method of sound location has many objections including the danger of body contact with rotating engine parts and hot exhaust ducts. Many areas of the engine and its associated systems which generate noise are difficult to reach in terms of hearing proximity and thus to pinpoint sound sources and causes. Further, it is often difficult to locate the source of a particular sound with this crude detection method because of echo effects and low level abnormal signals are masked by louder engine noises. Finally, certain abnormal sound vibrations may fall outside of the audible frequency range of a mechanic's hearing capacity.

A second commonly used engine sound discrimination method has involved the use of an elongated and flexible rubber or plastic tube of which one end is inserted into the mechanic's ear with the other tube end moved by hand to various areas and parts of the operating engine so as to isolate the source of a particular type of engine sound. This crude method also has disadvantages because the hand manipulated end of the sound tube cannot be brought into close proximity to hot pipes, ducts and surfaces of the engine system or to rotating engine parts without the danger of injury to the mechanic's hand. Also, there is the drawback of this method that certain types of acoustic signals may not couple effectively with the hand-held, open end of the sound tube or propagate through the interior of the tube without sound energy loss so that the signals are not detectable at the ear end of the tube.

Another classic and crude method for engine noise discrimination, particularly used to find the source of a screeching sound which usually indicates a faulty bearing in a water pump, alternator, air conditioner compressor, or other rotating engine part, is for the mechanic to hold a screwdriver in his or her mouth and to contact the driver bit portion of the screwdriver to various parts of the engine system to feel for low level vibrations. Thus, engine system vibrations are transmitted through the screwdriver and mechanic's jawbone system to the ear where they can be detected without concern for masking by engine and engine compartment echoes. This method of noise detection also has numerous drawbacks and dangers including facial harm from rotating and hot engine parts and exposure of the mouth and eyes to engine dirt.

Eventually, auto mechanics recognized the value of the simple medical-type stethoscope as a device for detecting, locating and diagnosing sounds generated by internal combustion engines. In recent years the basic principals of the more sophisticated medical electronic stethoscope, for detecting and discriminating between human auscultatory sounds, have been applied to devices for detecting acoustical signals and sounds generated by engine systems. Thus, an electronic stethoscope with a sound probe (coupled to an earphone headset) for detecting automotive engine sounds to locate potential mechanical faults (valve chatter, tappet noise, piston slap, gear and pump noises, etc.) has been supplied to the professional auto maintenance field since 1987 by Transcat of Rochester, N.Y. In 1989 JS Products, Inc. of Las Vegas, Nev. introduced the "EngineEAR" as an improved electronic stethoscope or listening tool for use by the automotive maintenance profession. This device included a sensitive microphone at the tip end of an extended flexible probe arm.

It is a principal object of the present invention to provide a new and improved acoustic signal and sound diagnostic tool for the professional automotive engine and industrial machinery maintenance field to detect with greater sensitivity and accuracy the existence, location and cause of operating engine and machinery abnormalities and engine and machinery environmental abnormalities.

It is a further object of the invention to provide a new and improved electronic listening tool for the professional engine and machinery mechanic which is capable of discriminating with greater sensitivity the acoustic signals and sounds forming the noise patterns of operating engines and machinery and to locate the source of and cause of such signals and sounds.

It is a still further object of the invention to provide a new and improved acoustic signal and sound diagnostic instrument with an ultra-sensitive, transducer-type sound pick-up at the tip of an extended flexible and positionable probe arm (for direct contact with operating engine and machinery parts) coupled through electronic circuitry to an earphone headset for audible sound discrimination and to visual means for indicating changes and peaks in sound level and average values of sound level.

Other objects and advantages of the invention will be apparent to those skilled in the professional engine and machinery maintenance field from the following summary and detailed description of the acoustic signal and sound diagnostic instrument of the invention taken together with the accompanying drawing figures.

SUMMARY OF THE INVENTION

The present invention relates to an improved electronic acoustic signal and sound detection and diagnostic tool for the professional automotive engine and industrial machinery maintenance field to detect with greater sensitivity and accuracy the existence, location and cause of operating engine and machinery abnormalities. In accordance with the invention an acoustic transducer, for receiving and converting an acoustic signal or sound of an operating engine or machine into an electromagnetic signal, is mounted at the forward sound pick-up end of an elongated deformable, semi-rigid probe arm of the diagnostic tool. The rearward end to the probe arm is mounted to the electronics housing of the tool. The transducer is preferably provided with directional sensitivity so as to permit the maintenance operator using the tool to localize the point of origin of the acoustic signal. The semi-rigid probe arm is deformed into a desired shape and maneuvered by the operator to bring the pick-up end of the probe arm and transducer to a preselected listening position proximate the operating engine or machine.

The electronics housing of the sound diagnostic tool of the invention includes an integrated circuit preamplifier, calibration circuitry for the visual means (pointer-type decibel meter) for indicating changes and peaks in sound level, a multi-point range selector, and frequency curve selector all electrically interconnected to the acoustic transducer. The electronics housing also includes an integrated circuit operational amplifier electrically interconnected to the preamplifier circuitry and range selector through a volume control device with electromagnetic signal output of the operational amplifier fed to an earphone headset.

The decibel meter visual means for indicating changes and peaks in sound level is mounted to the face side of the electronics housing and is electrically interconnected to a fast-slow response selector whereby in the fast mode the meter reacts quickly to changes in sound level giving an indication of peak sound levels and whereby in the slow mode the meter is dampened and indicates an average value of sound level. A rotary switch operates the range selector and allows the operator to select one of seven sound level ranges, each spanning 16 decibels. A weighting curve selector interfaces with the preamplifier circuitry with a "C" curve select position being nearly uniform over the sound frequency range of 32 to 10,000 hertz and with an "A" curve select position responding to sound frequencies in the 500 to 10,000 hertz range, the latter being the frequency range of greatest receptivity for the human ear. The output of the preamplifier section of the electronic listening tool of the invention is provided with a jack receptacle for permitting the interconnection of a cassette recorder-player to the circuitry of the tool. A 9 volt rechargeable battery powers the sound detection and diagnostic tool of the invention.

Through the present invention an improved acoustic signal and sound diagnostic instrument is provided for professional engine and machinery maintenance personnel, particularly automotive repair mechanics. The instrument is ultra-sensitive to sound types and levels and is thus capable of discriminating with great accuracy the acoustic signals and sounds forming the noise patterns of operating engines and machinery and thereby detecting and locating operating engine and machinery abnormalities through the hearing capabilities of the professional mechanic. Sound diagnosis is not only performed by the hearing capabilities of the mechanic operator of the instrument but also by visual observation by the operator of meter indications of sound levels within selected ranges with instrument adjustability to obtain optimum sensitivity of sound level readings.

BRIEF DESCRIPTION OF THE DRAWING FIGURES

FIG. 1b is a right side elevation view of the electronics housing of the instrument of FIG. 1a;

FIG. 1c is a left side elevation view of the electronics housing of the instrument of FIG. 1a.

DETAILED DESCRIPTION OF A PREFERRED EMBODIMENT OF THE INVENTION

Figure 1:
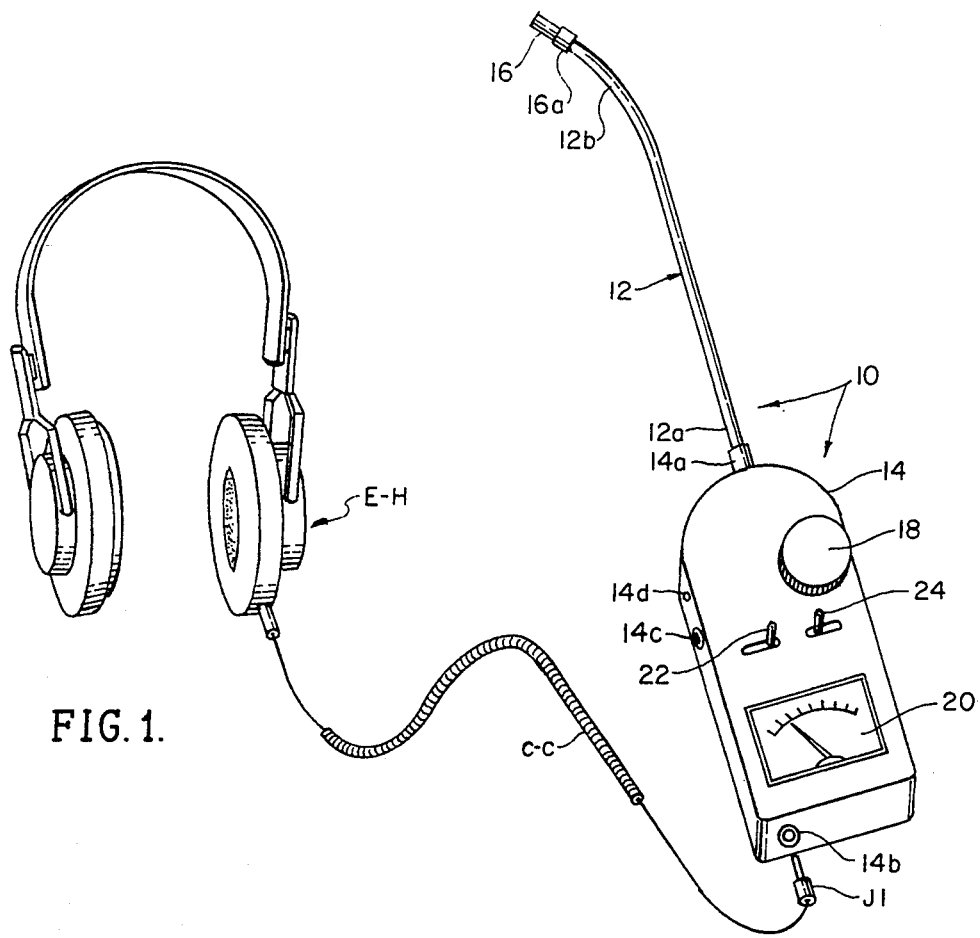
FIG. 1 is a perspective view of the acoustic signal and sound diagnostic instrument (with an associated earphone headset) of the present invention showing the elongated deformable sound pick-up prob arm attached to the electronics housing of the instrument.

Turning now to the drawings, and initially to FIG. 1, the acoustic signal and sound diagnostic instrument of the present invention is shown in a perspective view and is generally designated as a whole by reference numeral 10. The instrument 10 is comprised of an elongated semi-rigid probe arm 12 (deformable into a wide latitude of shapes) mounted at its rearward end 12a to, and extends from, an electronics housing 14. Mounted at the forward sound pick-up end 12b of the probe arm 12 is a shielding sleeve 16 which contains an acoustic transducer (shown in the schematic circuit diagram of FIG. 2). The shielding sleeve 16 is preferably made of a semi-flexible heat resistant material such as is used to form the terminal covers of spark plug cables (a pliable and sound absorbing or dampening material such as heat resistant neoprene, rubber or foam plastic) so that the sleeve can be pressed directly onto hot exterior portions or parts of an operating engine or machine. The shielding sleeve acts as an acoustic sound guide and shield for the enclosed acoustic transducer and provides the transducer with directional sensitivity. The sleeve 16 also shields the transducer from acoustic noise sources located outside of the open end thereof and protects the transducer from dirt and physical abuse.

The semi-rigid, deformable probe arm 12 may be comprised of a tube formed of a spirally wound length of ductile metallic ribbon wrapped about a helical spring. A flexible insulating plastic sheath covers the spirally wound metallic tube to prevent accidental shorting of electrical terminals with which the probe arm may come into accidental contact during the maneuvering of the diagnostic instrument 10 near an operating engine or machine.

The acoustic transducer located within the shielding sleeve 16 at the forward end of the probe arm 12 may be, for example, an "ELECTRET" condenser type microphone as marketed by Radio Shack or other known sound pick-up device. It is mounted within the shielding sleeve 16 out of contact with the spirally wound metallic tube of the probe arm and is electrically interconnected to the circuitry within the electronics housing 14 (see circuitry diagram of FIG. 2). A linking portion 16a of the shielding sleeve 16 mechanically connects such sleeve (and internal transducer) to the pick-up end 12b of probe arm 12 and acts an acoustic insular, or for isolating the transducer from the probe arm. For optimum results it has been found that the transducer should be located approximately one inch away from the pick-up end 12b of the probe arm and also approximately one inch away from the front opening of the shielding sleeve 16.

A coupling member 14a of the electronics housing 14 receives and mounts the rearward end 12a of the probe arm 12 to the housing. The coupling member 14a may be of such design as to permit the probe arm 12 (and its internal electrical circuit leads from the transducer to the circuitry of the electronics housing) to be removably mounted to the housing so that the probe arm may be replaced if damaged.

The electronics housing 14 of the acoustic signal and sound diagnostic instrument 10 of the invention is preferably of a shape and size such that it can be easily held in the hand of the mechanic operator. As shown in its perspective view in FIG. 1, the front face of electronics housing 14 includes a thumb operated rotatable sound level range selector control 18, a sound level decibel (dB) meter 20, a two position weighting selector control switch 22, and a two position response selector control switch 24. The electronics housing 14 of the instrument 10 (and its internal circuitry as described hereinafter) is interconnected to an earphone headset E-H via a coiled cable C-C and cable jack J1 which is plugged into the jack receptacle 14b of the housing 14.

Figure 1C:
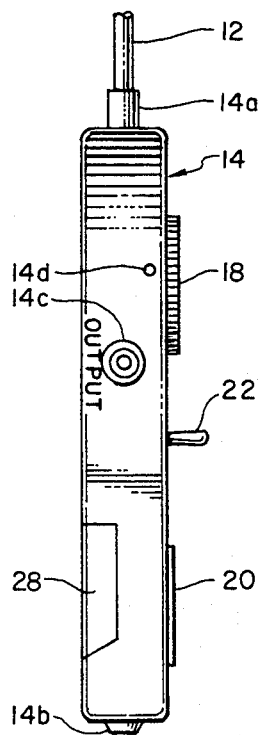
Figure 1A:
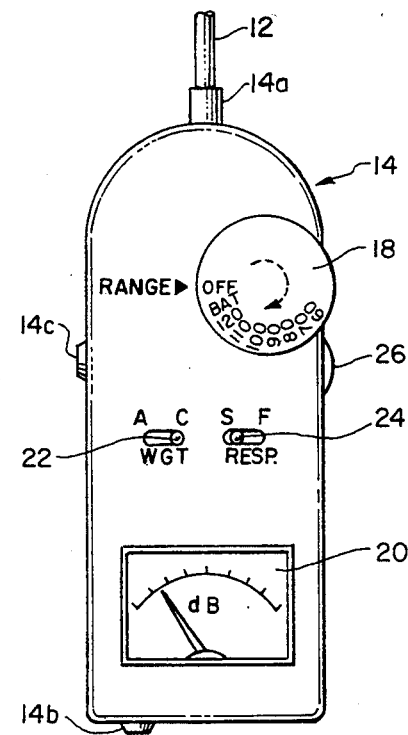
FIG. 1a is a front elevation view of the electronics housing of the acoustic signal and sound diagnostic instrument of FIG. 1 showing in greater detail the sound range controls and visual sound level meter of the instrument.

A more specific view of the front face of housing 14 is shown in FIG. 1a. The rotatable range selector control 18 lets the operator select one of seven sound levels, each spanning 16 dB. As shown in FIG. 1a the range selector 18 is in its "off" position and may be rotated clockwise in steps first to a battery "on" (and battery check) position followed by the seven center-point range value settings (120, 110, 100, 90, 80, 70 and 60 dB). The needle indicator of the sound level decibel meter 20 shows the actual sound level as a displacement from the center-point of the meter scale, Thus, for example, if the range selector 18 is set to 80 dB, and the meter scale reads −3 the actual sound level is 80 minus 3 or 77 dB.

The two position response selector control switch 24 has a slow position "S" and a fast position "F". With the response selector switch 24 in the slow position "S" the decibel meter 20 is damped and indicates an average-value sound level. With the switch 24 in the fast position "F" the decibel meter reacts quickly to a change in sound level giving the operator an immediate visual indication of peak sound levels present in the environment of the transducer (microphone) sound pick-up of the probe arm 12. The two position weighting curve selector control switch 22 has an "A" curve position and a "C" curve position. In the "C" curve position the C-weighting curve is nearly uniform over the sound frequency range of 32 to 10,000 Hz thus giving an indication of overall sound level. In the "A" curve position the A-weighting characteristic responds primarily to frequencies in the 500 to 10,000 Hz range which is the area of greatest sensitivity of the human ear.

Figure 1B:
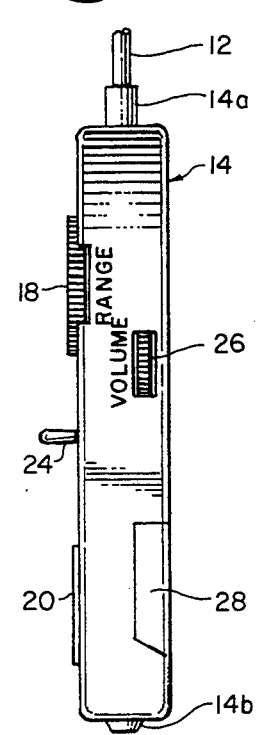
Figure 2:
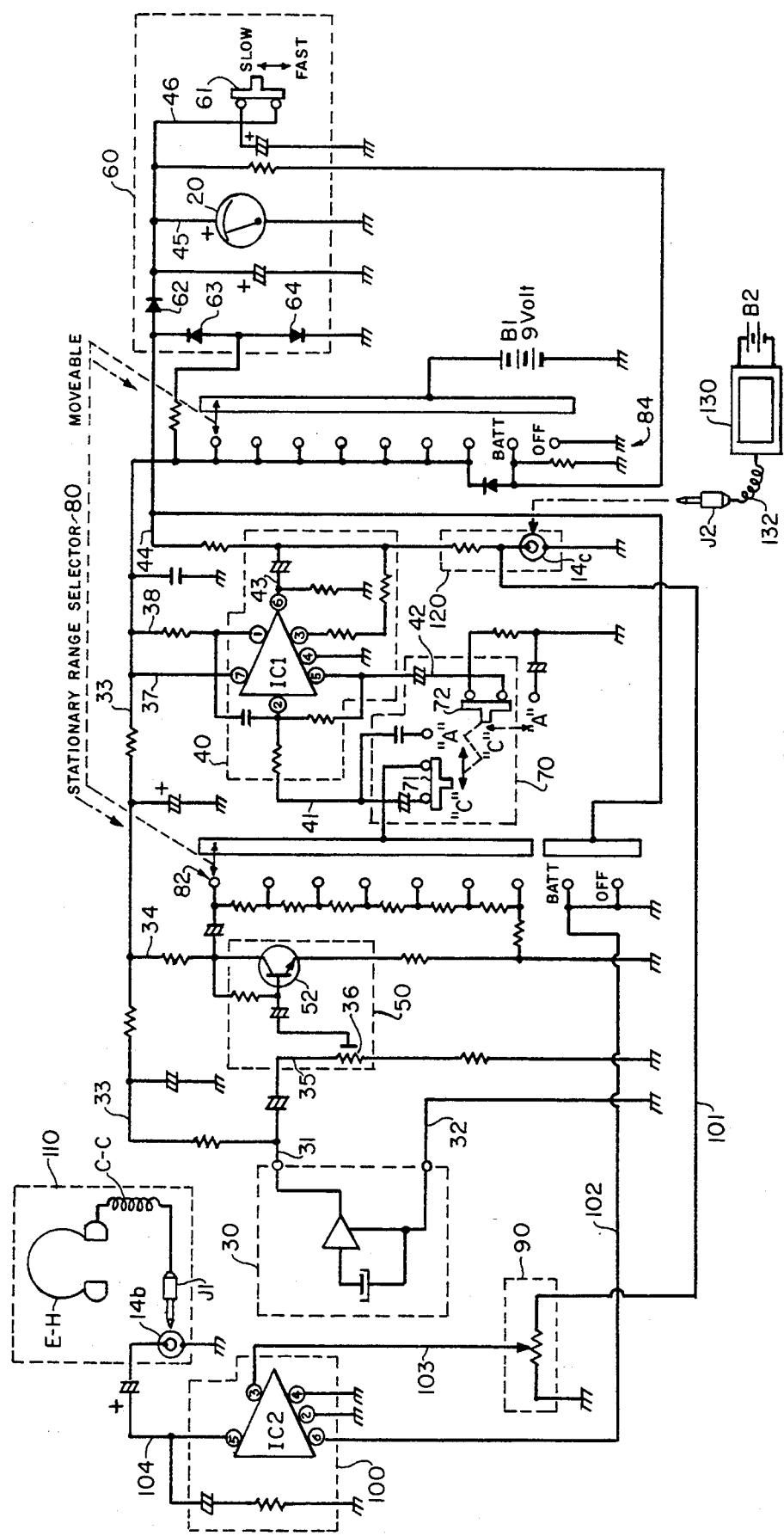
FIG. 2 is an electrical schematic circuit representation of the electronic acoustic signal and sound diagnostic instrument of the invention.

In FIGS. 1b and 1c right side and left side elevation views, respectively, are shown of the electronics housing 14. In the FIG. 1b right side elevation view there is shown a thumb operated rotatable volume controller 26 for regulating the sound volume level transmitted by the sound diagnostic instrument 10 to the earphone headset E-H which is worn by the mechanic operator of the instrument and which is interconnected to the electronics housing 14 via coiled cable C-C. In the FIG. 1c left side elevation view there is shown a jack receptacle 14c for receiving a jack j2 (not shown) which may be utilized to interconnect a cassette-type recorder-player unit to the sound output circuitry within the electronics housing 14 as shown in FIG. 2. In such figure there is also shown an access port 14d through which a calibrating tool may be inserted to adjust the instrument, if required. In both FIGS. 1b and 1c there is shown the right and left ends, respectively, of the battery compartment cover 28 which removably closes the battery compartment containing the 9-volt battery power supply for the sound diagnostic instrument 10 of the invention.

Referring now to FIG. 2, there is illustrated an electrical schematic circuit representation of the electronic acoustic signal and sound diagnostic instrument of the present invention. The principal functional areas of circuitry are outlined by numbered dash-line enclosures as follows:

30—Acoustic transducer microphone located in the shielding sleeve 16 of the probe arm 12.
40—Pre-amplifier circuitry located in the electronics housing 14.
50—Calibration circuitry located in the electronics housing 14.
60—Sound level decibel meter and response selector located on and within the electronics housing 14.
70—Weighting curve selector located on and within the electronics housing 14.
80—Range selector located on and within the electronics housing 14.
90—Volume control located on and within the electronics housing 14.
100—Operational amplifier located within the electronics housing 14.
110—Headphone and headphone jack located outside of the electronics housing 14.
120—Output circuitry and jack receptacle for cassette recorder-player.

The acoustic transducer microphone 30, located in the shielding sleeve 16 at the forward end 12b of the probe arm 12, is interconnected through leads 31 and 32 (ground) within the probe arm to the pre-amplifier circuitry 40, instrument calibration circuitry 50 and circuitry of the stationary terminal set 82 and moveable terminal set 84 of the range selector 80. More specifically, the calibration circuitry (including npn bipolar transistor 52) is connected to microphone lead 31 via circuit line 33 and lead 34 and via circuit line 35 to the variable resistor 36 of the calibration circuitry and thereafter to ground. Circuit line 33 also connects the integrated circuit microchip IC1 of the preamplifier circuitry 40 (via leads 37 and 38) to the transducer microphone 30. Finally, circuit line 33 connects the transducer microphone to the battery "on" contact and seven switch position contacts of the moveable terminal set 84 and the battery "on" contact and seven switch position contacts of the stationary terminal set 82 of the range selector 80.

The pre-amplifier circuitry 40 interacts with the weighting curve selector 70 through leads 41 and 42 from the microchip IC1 with the weighting curve selector switch 22 (see FIG. 1a) moving the switch contacts 71 and 72 from switch terminals "A" to switch terminals "C". The pre-amplifier circuitry 40 also interacts with the sound level decibel meter and response selector circuitry 80 via circuit lines 43 and 44 from the microchip IC1. When the response selector 61 is in the "Slow" position the decibel meter 20 is damped and indicates an average-value sound level whereas when the selector 61 is in the "Fast" position the meter 20 reacts quickly to a change in sound level giving an indication of peak sound levels present in the environment of the transducer microphone 30. The decibel meter is connected to circuit line 44 of the pre-amplifier circuitry via lead 45 with the response selector 61 interconnected to circuit line 44 via lead 48. The sound level decibel meter and response selector circuitry 60 also includes rectifiers 62, 83 and 64.

A 9 volt battery B1 energizes the electronic circuitry within the electronics housing 14. The pre-amplifier circuitry 40, calibration circuitry 50 and range selector circuitry 80 are electrically interconnected to operational (audio) amplifier circuitry 100 via circuitry lines 101 and 102. Circuitry line 101 interconnects to the integrated circuit microchip IC2 of the operational amplifier circuitry 100 via lead 103 through the volume control 90. Circuitry line 102 interconnects directly to the microchip IC2 of the amplifier circuitry 100. The audio signal output of operational amplifier circuitry 100 feeds the headphone and headphone jack unit 110 which includes headphone jack receptacle 14b, located in the electronics housing 14 of sound diagnostic instrument 10 of the invention, and into which the jack J1 may be plugged with interconnection to earphone headset E-H via coiled cord C-C.

It will be noted that the circuitry line 101 leading from the pre-amplifier circuitry 40 to the volume control 90 and operational amplifier 100 includes output circuitry 120 and jack receptacle 14c (located in the electronics housing 14). This output circuitry provides access to the sound patterns and sound levels picked up by the transducer microphone 30 of the instrument 10 for recordation via a cassette type recorder-player unit 130 interconnected to jack receptacle 14c via a coiled cord 132 and jack connector J2. Energization of the recorder-player unit 130, for replay of the recorded sound patterns, may be a battery B2 or by connection of the unit 130 to the low voltage output of an automobile cigarette lighter.

Through the present invention acoustic signals and sounds generated by automotive engines and industrial machinery can be detected, located and diagnosed with greater sensitivity and accuracy. The diagnostic instrumentation of the invention permits accurate audible sound discrimination and diagnosis through an earphone headset worn by a professional maintenance operator and by visual decibel meter means indicating with great sensitivity changes and peaks in sound level and average values of sound level generated by abnormalities in engine and machinery operation.

While a preferred embodiment of the present invention has been disclosed herein and illustrated in the accompanying drawing figures, it will be apparent to one skilled in the art that many variations and modifications may be made without departing from the scope and spirit of the invention as defined by the following claims.

What I claim is:

1. An acoustic signal and sound diagnostic instrument for discriminating audible automotive engine and industrial machinery abnormalities for use by a professional maintenance operator comprising:
   a) an elongated deformable, semi-rigid probe arm bearing an acoustic transducer microphone at the forward end thereof for detecting and converting audible acoustic signals and sounds having a frequency in the range of from about 500 to about 10,000 Hz into electromagnetic signals;
   b) an electronics housing conformed to be held in the hand of said maintenance operator, said housing mechanically connected to and supporting said probe arm at the rearward end thereof;
   c) pre-amplifier circuitry within said housing electrically coupled to said transducer microphone for receiving said electromagnetic signals from said microphone;
   d) range selector circuitry within said housing for selecting sound level ranges respecting said electromagnetic signals;
   e) a decibel meter mounted to the exterior of said housing and electrically interconnected to said pre-amplifier circuitry for visually indicating changes and peaks in the sound levels detected by said transducer microphone;
   f) operational audio amplifier circuitry within said housing electrically interconnected to said pre-amplifier circuitry for converting said electromagnetic signals into secondary audible acoustic signals;
   g) a battery power supply electrically interconnected to said range selector circuitry and said pre-amplifier circuitry for energizing said instrument; and
   h) an earphone headset electrically interconnected to said audio amplifier circuitry for use by said operator whereby said secondary audible acoustic signals are available to said operator for audible discrimination of engine and machinery abnormalities.

2. The acoustic signal and sound diagnostic instrument as claimed in claim 1 wherein the pre-amplifier circuitry has associated therewith a weighting curve selector with a "C" curve select position providing substantially uniform sound levels over the frequency range of from 32 to 10,000 Hz and with an "A" curve select position providing maximum sensitivity of human ear response to frequencies in the 500 to 10,000 Hz range.

3. The acoustic and sound diagnostic instrument as claimed in claim 1 wherein the decibel meter has electrically associated therewith a response selector switch having a first slow position whereby said meter is damped and indicates an average-value of the sound levels detected by said transducer microphone and a second position whereby said meter reacts quickly to a change in the sound levels detected by said transducer microphone and indicates peak sound levels in the environment of said microphone.

4. The acoustic and sound diagnostic instrument as claimed in claim 1 wherein the range selector circuitry interconnected to said pre-amplifier circuitry includes a rotatable control switch having an "off" position for terminating operation of the instrument, a battery "on" and check position for operation of the instrument, and a multiplicity of center-point decibel value range setting positions.

5. The acoustic and sound diagnostic instrument as claimed in claim 4 wherein the center-point decibel value range setting positions of the rotatable control switch of the range selector circuitry are 120, 110, 100, 90, 80, 70 and 60 decibels.

6. The acoustic sound diagnostic instrument as claimed in claim 1 wherein the pre-amplifier circuitry electrically interconnected to the operational audio amplifier circuitry includes access means for interconnecting a recorder-player device for recording the sound patterns and sound levels picked up by said transducer microphone.

7. An acoustic signal and sound diagnostic instrument for use by professional automotive engine and industrial machinery maintenance operators for locating and discriminating audible automotive engine and industrial machinery abnormalities comprising:
   a) an elongated deformable, semi-rigid probe arm bearing an acoustic transducer microphone at the forward end thereof for detecting and converting audible acoustic signals and sounds having a frequency in the range of from about 500 to about 10,000 Hz into electromagnetic signals;
   b) an electronics housing conformed to be held in the hand of said maintenance operator, said housing mechanically connected to and supporting said probe arm at the rearward end thereof;
   c) pre-amplifier circuitry within said housing and electrically interconnected via leads extending through said probe arm to said transducer microphone for receiving said electromagnetic signals from said microphone;
   d) range selector circuitry within said housing electrically interconnected to said pre-amplifier circuitry and operable by a rotatable control switch having a thumb operated selector dial mounted to the outside of said housing, said rotatable control switch of the range selector circuitry having an "off" position for terminating operation of the instrument, a battery "on" and check position for indicating operation of the instrument, and a multiplicity of center-point decibel value range setting positions;
   e) a decibel meter mounted to the exterior of said housing and electrically interconnected to said pre-amplifier circuitry for visually indicating changes and peaks in the sound levels detected by said transducer microphone;
   f) operational audio amplifier circuitry within said housing electrically interconnected to said pre-amplifier circuitry for converting said electromagnetic signals into secondary audible acoustic signals;
   g) a battery power supply electrically interconnected to said range selector circuitry and said pre-amplifier circuitry for energizing said instrument when the rotatable control switch of said range selector circuitry is turned to said battery "on" position; and
   h) an earphone headset electrically interconnected to said audio amplifier circuitry for use by the operators of said instrument for audible discrimination of engine and machinery abnormalities, 8. The acoustical signal and sound diagnostic instrument as claimed in claim 7 wherein the rotatable control switch of the range selector circuitry includes center-point decibel value range setting positions of 120, 110, 100, 90, 80, 70 and 60 decibels.

9. The acoustical signal and sound diagnostic instrument as claimed in claim 7 wherein the pre-amplifier circuitry has electrically interconnected therewith a weighting curve selector with a "C" curve select position providing substantially uniform sound levels to said operational audio amplifier circuitry over the frequency range of from 32 to 10,000 Hz and with an "A" curve select position providing maximum sensitivity of human ear response to frequencies in the 500 to 10,000 Hz range.

10. The acoustic signal and sound diagnostic instrument as claimed in claim 7 wherein the pre-amplifier circuitry electrically interconnected to the operational audio amplifier circuitry includes access means for interconnecting a recorder-player device for recording the sound patterns and sound levels picked up by said transducer microphone.

11. The acoustic signal and sound diagnostic instrument as claimed in claim 7 wherein the operational audio amplifier circuitry is provided with volume control means.

* * * * *